(12) United States Patent
Suarez-Rivera et al.

(10) Patent No.: US 11,073,463 B2
(45) Date of Patent: Jul. 27, 2021

(54) METHODS FOR MODELING PERMEABILITY IN LAYERED ROCK FORMATIONS

(71) Applicant: W.D. Von Gonten Laboratories, LLC, Houston, TX (US)

(72) Inventors: Roberto Suarez-Rivera, Houston, TX (US); William D. Von Gonten, Jr., Houston, TX (US); Safdar Ali, Houston, TX (US); John Degenhardt, Houston, TX (US); Bradley Abell, Houston, TX (US)

(73) Assignee: W.D. Von Gonten Laboratories, LLC, Houston, TX (US)

( * ) Notice: Subject to any disclaimer, the term of this patent is extended or adjusted under 35 U.S.C. 154(b) by 198 days.

(21) Appl. No.: 16/413,249

(22) Filed: May 15, 2019

(65) Prior Publication Data
US 2019/0353574 A1 Nov. 21, 2019

Related U.S. Application Data

(60) Provisional application No. 62/671,733, filed on May 15, 2018.

(51) Int. Cl.
  *G01N 15/08* (2006.01)
  *G01N 33/24* (2006.01)
(52) U.S. Cl.
  CPC .......... *G01N 15/082* (2013.01); *G01N 33/24* (2013.01); *G01N 2015/0846* (2013.01)

(58) Field of Classification Search
  CPC ...... G01N 15/00; G01N 15/08; G01N 15/082; G01N 33/24; G01N 2015/0846
  See application file for complete search history.

(56) References Cited

U.S. PATENT DOCUMENTS

| | | | |
|---|---|---|---|
| 8,538,700 B2 * | 9/2013 | Badri | G01V 3/38 702/7 |
| 9,348,056 B2 * | 5/2016 | Fredrich | G01N 33/24 |
| 2007/0276639 A1 * | 11/2007 | Montaron | G01V 11/00 703/10 |
| 2010/0095742 A1 * | 4/2010 | Symington | E21B 41/0064 73/23.35 |
| 2010/0313633 A1 * | 12/2010 | Anand | G01V 3/32 73/38 |
| 2013/0259190 A1 * | 10/2013 | Walls | G01N 33/24 378/9 |
| 2016/0169856 A1 * | 6/2016 | Sung | G01V 8/02 703/10 |

* cited by examiner

*Primary Examiner* — Nguyen Q. Ha

(57) ABSTRACT

Methods for simulating the movement of fluid through a formation volume comprises defining a lab-scale model representing rock fabric and associated permeability along a single well location within a formation volume and converting the lab-scale model to a field-scale model representing rock fabric and associated permeability at the single well location. The field-scale model representing rock fabric and associated permeability is correlated with field-scale log data and interpolated between multiple well locations so as to create a field-scale model representing rock fabric and associated permeability across the formation volume so that the movement of fluid through the formation volume can be simulated.

20 Claims, 3 Drawing Sheets

METHODS FOR MODELING PERMEABILITY IN LAYERED ROCK FORMATIONS

This application claims the benefit of U.S. provisional patent application Ser. No. 62/671,733 filed on May 15, 2018, which is incorporated herein by reference.

BACKGROUND

The disclosure relates generally to methods for earth modeling. More particularly, this disclosure relates to modeling permeability (or hydraulic conductivity) in layered rock formations to support the prediction of fluid flow within the formation.

The laboratory-measured permeability of reservoir mudstones is often in the 10 to 100 nanodarcy range. However, observed field evidence, such as from fluid leak-off during hydraulic fracturing, suggests that the actual permeability of the layered formations containing those mudstones is considerably higher. High permeability in layered formations can reduce the effectiveness of hydraulic fracturing and have detrimental effects on other wells in the same formation. Thus, understanding the permeability of a layered rock formation and how that permeability impacts well drilling and completion has become an important factor in developing many hydrocarbon reservoirs.

Some have proposed that field-observed permeability is primarily controlled by a subset of microcracks that are formed during hydraulic fracturing. These microcracks enhance the natural permeability of the formation in the region immediately surrounding the hydraulically fractured portion of the formation. One limitation of the microcrack theory is that the region with enhanced permeability is necessarily localized to the area impacted by hydraulic fracturing. This necessary localization often fails to explain the interaction between offset wells or the effect on subsequent wells in the same area (parent-child well relationships) that are outside of the localized regions.

Others theorize that naturally-occurring fractures within the formation contribute to a higher field-observed permeability. These naturally-occurring fractures provide fluid communication in the formation such that the density of naturally-occurring fractures in an area is proportional to the area's permeability. In order to support the field-observed permeability, a high density of naturally-occurring fractures must exist across the entire field, but, in order to retain fluids within the reservoir, the naturally-occurring fractures would have to be contained within the reservoir so as to prevent communication with non-reservoir sections. Naturally-occurring fractures exhibiting this type of behavior are uncommon.

Thus, there remains a need in the art for methods to model permeability in a layered formation that can be used to predict fluid flow and production of hydrocarbons from that formation as multiple wells are drilled and completed over a period of time.

BRIEF DESCRIPTION

A method for simulating the movement of fluid through a formation volume comprises defining a lab-scale model representing rock fabric and associated permeability along a single well location within a formation volume and converting the lab-scale model to a field-scale model representing rock fabric and associated permeability at the single well location. The field-scale model representing rock fabric and associated permeability is correlated with field-scale log data so that additional field-scale models representing rock fabric and associated permeability can be defined at other well locations within the formation volume using the correlated field-scale log data from the other well locations. The field-scale model representing rock fabric and associated permeability is then interpolated between the single well location and the other well locations so as to create a field-scale model representing rock fabric and associated permeability across the formation volume and the movement of fluid through the formation volume is simulated.

In certain embodiments, defining a lab-scale model representing rock fabric and associated permeability further comprises measuring a plurality of properties along a core sample at lab-scale resolution and identifying and classifying a plurality of layers and interfaces along the core sample. A permeability is associated to each of the plurality of layer and interface classifications and the plurality of measured properties are integrated with the plurality of layer and interface classifications and associated permeability to create the lab-scale model representing rock fabric and associated permeability. The plurality of properties may include one or more of computed tomography density; gamma ray density, electrical resistivity, acoustic velocity, gamma ray components, magnetic susceptibility, rock hardness, and X-ray fluorescence elemental composition. The field-scale log data includes one or more of electrical properties, sonic properties, nuclear measurements, and pressure measurements. In certain embodiments, the movement of fluid through the formation is simulated during a completion operation or during production. In some embodiments, the method further comprises updating the lab-scale model of the formation volume based on the movement of fluid through the formation volume.

A method for simulating the movement of fluid through a formation volume comprises defining a lab-scale rock fabric model at a single well location within a formation volume and converting the lab-scale rock fabric model to a field-scale rock fabric model. Both the lab-scale rock fabric model and field-scale rock fabric model include permeability per unit depth. The field-scale rock fabric model is correlated with field-scale log data so that the field-scale rock fabric model can be interpolated across the formation volume using field-scale log data at other well locations within the formation volume so that the movement of fluid through the formation volume can be simulated.

In certain embodiments, defining the lab-scale rock fabric model further comprises measuring a plurality of properties along a core sample at lab-scale resolution and identifying and classifying a plurality of layers and interfaces along the core sample. Each of the plurality of layer and interface classifications are associated with a permeability, which is integrated with the plurality of measured properties and layer and interface classifications to create the lab-scale rock fabric model. The plurality of properties may include one or more of computed tomography density; gamma ray density, electrical resistivity, acoustic velocity, gamma ray components, magnetic susceptibility, rock hardness, and X-ray fluorescence elemental composition. The field-scale log data includes one or more of electrical properties, sonic properties, nuclear measurements, and pressure measurements. In certain embodiments, the movement of fluid through the formation is simulated during a completion operation or during production. In some embodiments, the method further comprises updating the lab-scale model of the formation volume based on the movement of fluid through the formation volume.

A method for simulating the movement of fluid through a formation volume may also comprise measuring a plurality of properties along a core sample at lab-scale resolution. A plurality of layers and interfaces are identified and classified along the core sample and then associated with a permeability. The plurality of measured properties are integrated with the plurality of layer and interface classifications and associated permeability to create a lab-scale rock fabric model that can be converted into a field-scale rock fabric model. The field-scale rock fabric model is correlated with field-scale log data so that the field-scale rock fabric model can be interpolated across the formation volume using field-scale log data at other well locations within the formation volume so that the movement of fluid through the formation volume can be simulated.

The plurality of properties include one or more of computed tomography density; gamma ray density, electrical resistivity, acoustic velocity, gamma ray components, magnetic susceptibility, rock hardness, and X-ray fluorescence elemental composition. The field-scale log data includes one or more of electrical properties, sonic properties, nuclear measurements, and pressure measurements. In certain embodiments, the movement of fluid through the formation is simulated during a completion operation or during production. In some embodiments, the method further comprises updating the lab-scale model of the formation volume based on the movement of fluid through the formation volume.

DRAWINGS

Embodiments of methods for simulating the movement of fluid through a formation volume are described with reference to the following figures. Like numbers are used throughout the figures to reference like features and components.

DETAILED DESCRIPTION

It is to be understood that the following disclosure describes several exemplary embodiments for implementing different features, structures, or functions of the invention. Exemplary embodiments of components, arrangements, and configurations are described below to simplify the disclosure; however, these exemplary embodiments are provided merely as examples and are not intended to limit the scope of the invention.

The methods, or workflows, described in this disclosure are based around the theory that a dominant cause of leak-off and fluid migration in layered rock formations is the thinly laminated nature of these rocks and the contrasting properties between layers. The presence of thin layers of heterogeneous rock and the associated interfaces (collectively the "rock fabric") can lead to an increased permeability of reservoirs, simply due to its thinly laminated nature. Certain rock fabrics introduce a preferential directionality in the fluid flow that tends to increase permeability as a function of the lamination density, selected rock properties and the field-wide properties of pressure and stress. Thus, understanding the presence, distribution and properties of the rock fabric can help predict the larger-scale system permeability.

In general, the disclosed methods include defining a geomodel representing the system permeability of a layered formation volume by first modeling the existing rock fabric and permeability at a single location and then propagating that model across a formation volume or acreage. Once the rock fabric and permeability is determined, the acreage development can be simulated using a variety of known techniques to determine a preferable plan for developing the acreage. As the acreage is developed, the geomodel can be updated and adjusted to account for changes in the reservoir over time and the development plan altered as needed.

Building the geomodel that will produce reliable simulation results requires building a geomodel that represents the acreage as accurately as possible. This requires an understanding of the rock fabric present across the acreage as well as the critical properties of that rock fabric. The following discussion will focus on permeability as being a critical property but those skilled in the art will appreciate that other properties influencing the movement of fluid can, and will, be important and may also, or alternatively, be included as part of the geomodel. For purposes of this disclosure, "field-scale resolution" shall mean data with a resolution of one data point per foot or more and "lab-scale" resolution shall mean data with a resolution of one data point per centimeter or less.

Figure 1:
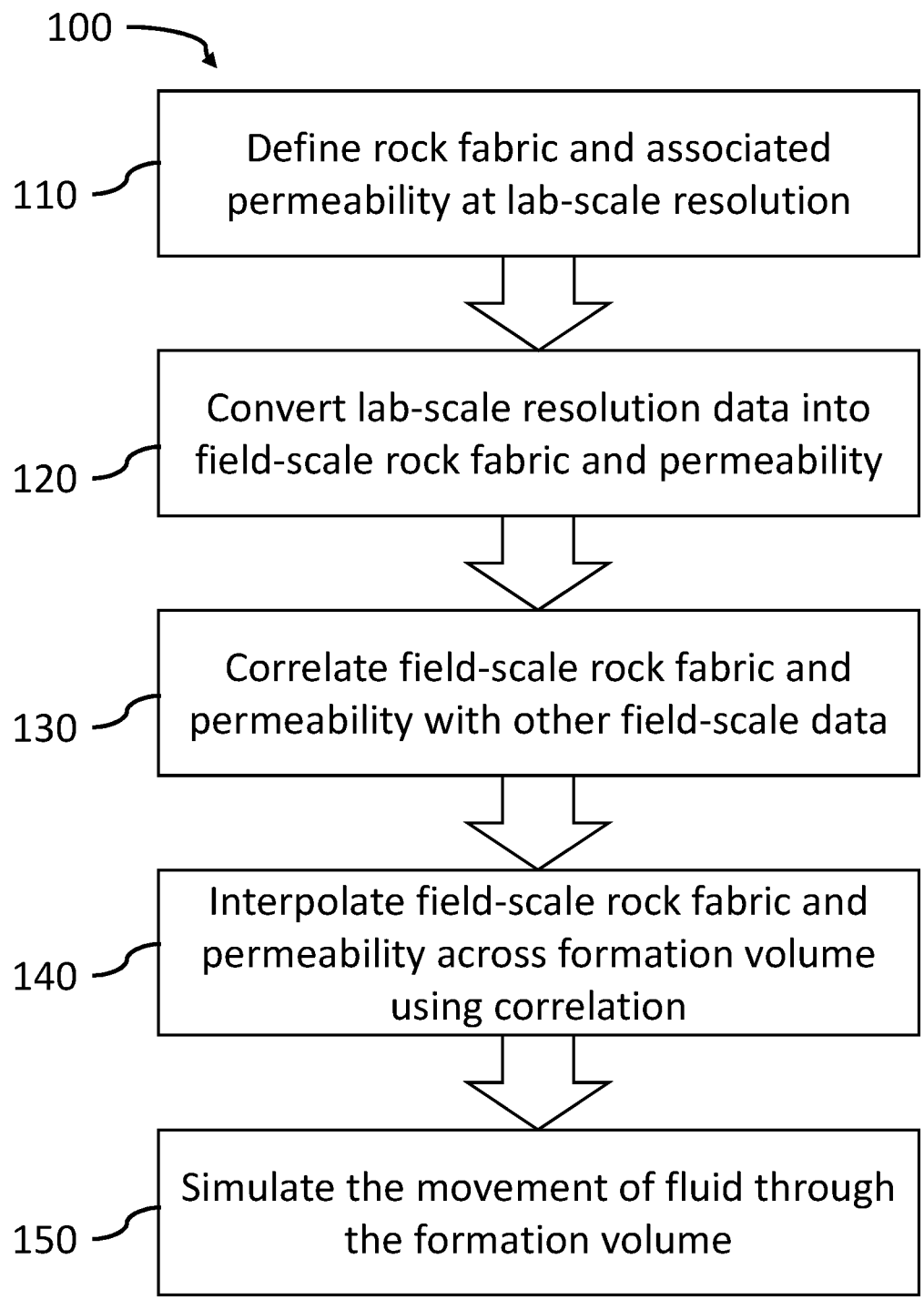
FIG. 1 illustrates a method for simulating the movement of fluid through a formation volume.

With reference to FIG. 1, a method 100 for simulating the movement of fluid through a formation volume may include first defining a rock fabric and associated permeability at lab-scale resolution 110. The lab-scale resolution data may be downscaled, or converted, into field-scale rock fabric data and properties 120, such as by applying a relational model or other mathematical methods. The field-scale rock fabric data and properties may be correlated with other field-scale data measurements 130, such as from petrophysical logging or other downhole measurements. Once the correlation is established, the field-scale rock fabric and associated permeability is then interpolated across a formation volume using the field-scale data measurements 140 to complete the geomodel. This interpolated data, as part of the geomodel, is used to predict the movement of fluid through the formation volume during hydraulic fracturing or production 150.

Figure 2:
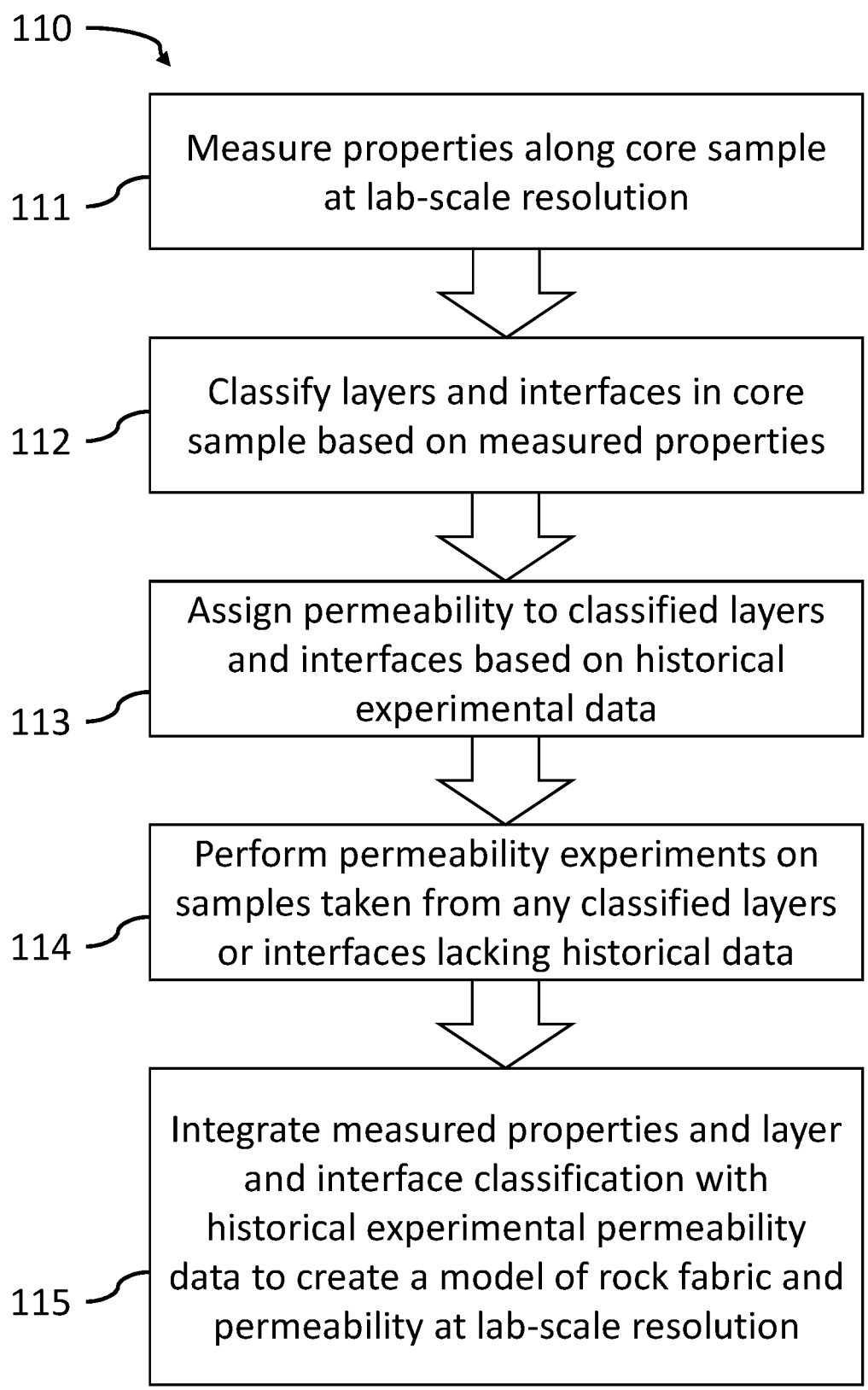
FIG. 2 illustrates a method for developing a lab-scale rock fabric model.

Referring now to FIG. 2, the first step in generating a lab-scale resolution rock fabric and the properties associate with that rock fabric 110 is to obtain core sections representative of the region of interest and perform an analysis of the core sections, including the measurement of properties at lab-scale resolution 111. These measured properties, and other geologic information, can be used to classify the layers and interfaces within the core sections 112. The classification of the layers and interfaces provides for a unique identifier to which a permeability may be associated either through application of historical experimental data 113 or through direct experimentation 114. The permeability data may be integrated with the measured properties and other layer or interface classification data to create a model of the rock fabric at lab-scale resolution including data representing permeability per unit depth 115.

These core sections may be taken from the acreage being evaluated and/or from other locations in the same reservoir and bounding units. The core section may include the entire height of formation being studied or smaller sections can be taken from multiple wells and then used to construct a combined vertical model core. The thin layers and interfaces can be analyzed using laboratory analysis of core samples, such as would be acquired from wells within the acreage.

Core analysis allows for the acquisition of lab-scale (cm or less resolution) data using specialized laboratory testing on core samples taken from depths of interest in the formation. The laboratory evaluation of a finely layered rock fabric allows for the identification and evaluation of every layer and interface, as well as their distribution and relationship with the geological processes acting in the region. The finely layered fabric, the contrasting properties between layers, and the associated system permeability can be measured on core samples by a combination of (i) lab-scale measurements along the length of the core; (ii) core geologic analysis; and (iii) selection of representative fabrics and interfaces for detailed measurements of permeability and interface strength.

The basic geologic attributes of a core section can be initially determined based on the pre-existing knowledge of the basin from which the sample was taken, visual review of the core sample, and initial laboratory testing. Existing prior knowledge of the basin and the dominant geologic processes active during basin development aid in the identification of the characteristic types of rock fabrics, thin layering, and associated interfaces in this basin. The laboratory testing can include lab-scale resolution measurements of multiple properties including (but not limited to): computed tomography density; gamma ray density, electrical resistivity, acoustic velocity, gamma ray components, magnetic susceptibility, rock hardness, X-ray fluorescence elemental composition and others, as necessary (depending on the rock fabrics thin layering, and associated interfaces that need to be identified).

Laboratory testing conducted on the core samples can further define their characteristic rock fabrics, thin layering, and interface attributes. The laboratory evaluation of a finely layered rock fabric allows for the identification, evaluation, and classification of every layer and interface, as well as their distribution and relationship with the geological processes acting in the region. These lab-scale measurements can be analyzed using multivariate classification techniques to define rock classes that are well and consistently differentiated by the high resolution measurements. These rock classes will represent the building blocks of the heterogeneous, thinly layered system, and allow the subsequent representation of characteristic rock fabrics with thin layering, by their representation with unique rock classes, or by the presence of interfaces between layers with contrasting properties, by their relationship with the boundaries between rock class couplets.

Data analytics can be applied to the lab-scale measurements to identify a subset of locations along the core sample from which additional sampling and analysis should be conducted. These samples can be selected based on the dominant set of rock fabrics and interfaces that needs to be identified and represented (e.g., ash beds, carbonate benches, fibrous veins, slickensides, a combination of them all, etc). By way of example, the additional sampling may be selected at locations (i) representative of the core section, of the distribution of rock classes and rock class couplets, and representative of the fabric and geologic attributes; (ii) based on heterogeneous rock analysis (HRA) classification; (iii) based on HRA couplet boundaries; (iv) based on geologic drivers and attributes; (v) based on rock fabric attributes derived from data analytics; (vi) based on an optimal number of samples to maximize the representation of all fabrics and their variability, along the core section or sections.

The additional analysis may be intended to provide additional description of relevant attributes of the rock fabric, thin layering and associated interfaces. These include, but are not limited to, fabric orientation, fabric flatness, fabric continuity, detachment characteristics, surface roughness (for detached interfaces), magnitude of the change in properties across the fabric or interfaces, sharpness of the change, and others, as may be indicated based on the type of the dominant interface (e.g., water sensitivity).

Additional specialized laboratory testing for mechanical and flow properties can also be conducted including shear test measurements on 1-in diameter to 1½-in diameter samples, for evaluation of friction and cohesion, along the preferential direction of weakness, as defined by the rock fabrics, thin layering, and associated interfaces. For intact interfaces, samples prepared at oblique orientations to the dominant rock fabric can be analyzed to evaluate shear failure and associated friction and cohesion properties. For samples with weaker fabric that has parted during coring or core handling, samples with the fabric oriented parallel to the axis of the plug, and the failed surface separate the sample in two equal pieces. Opposite-loading-pair end caps, which apply compression on half the loading area of the sample, on opposite sides at the two ends of the sample can be used to measure the amount of shear that is necessary for shear displacement at various levels of confinement. These, and other, measurements can also be used to determine the friction and cohesion along these interfaces.

When testing for permeability, fluid flow measurements can be taken along the directions parallel and perpendicular to the dominant rock fabrics, thin layering, and associated interfaces, at simulated in-situ effective stress conditions. This allows for a determination of the permeability associated to the thin layering and associated interfaces. The physical measurements of permeability of the representative samples may be correlated to their characteristic rock fabrics, fabric attributes, geologic attributes, rock classification, and rock class couplet boundaries. This correlation allows for the development of models that relate the physical properties of permeability to various rock fabrics.

The developed models may be applied to the entire section of core under investigation using statistical methods for propagation and cross validation. This provides high resolution representation of the rock fabric and permeability along the length of the core. If the statistical validation fails, select additional samples in the region with problems and test them, for increased representation and improved modeling.

These characterizations of discrete samples can be combined, or integrated, with high resolution measurements, geologic descriptions, rock classification methods, field logs, and other field-scale data to form a relational model between the field-scale data and lab-scale data. The field-scale data may include one or more of electrical properties, sonic properties, nuclear measurements, and pressure measurements. The lab-scale resolution representation of rock fabric and associated permeability along the core length can be used to develop homogenized models that downscale the relationships provide effective media equivalent values to represent rock fabric and associated permeability at field-scale resolution.

This field-scale resolution data may be correlated to field-scale log data so as to create models that allow for prediction of field-scale rock fabric and associated permeability data using field-scale data from other sources (such as petrophysical logs). Field-scale data is widely available, especially in formations and areas that are being developed as hydrocarbon resources. Although field-scale data provides valuable insights into the formation, in finely layered formations, the individual layers may only be inches thick, or less, and field-scale data may miss critical layers and interfaces.

Statistical methods for propagation and cross-validation can be used to apply and verify the model. If the model fails, additional field-scale information, such as additional field logs, can be utilized to improve the predictability of the model. The required type of field-scale information for adequate modeling will depend on the type of dominant rock fabrics and associated properties that one desires to recognize and propagate. This model then can be used to propagate the lab-scale permeability data along the logged section of vertical wells and, when multiple vertical wells with logs are available, across the region of interest. Mapping the system permeability in this manner helps us better understanding the variability in leak-off for hydraulic fracturing, the potential connectivity to other wells during hydraulic fracturing (well hits), and to better understand the influence of hydraulic fracturing by parent wells on subsequent child wells. This regional scale mapping of the system permeability also allow us to better understand variability in field production and pressure depletion across the region of interest.

These field-scale models may be used to propagate the rock fabric and associated permeability data through other sections where the appropriate field-scale data is available. For example, the model can be applied to multiple logs in a region to understand the regional distribution of rock fabric and associated permeability at the various well locations. The rock fabric and associated permeability data can also be interpolated between well locations and across depths using various statistical techniques. This can be used to create a representative volume (a "geomodel") of the rock fabric and associated permeability across the region and indicate the lateral and vertical variability of the rock fabric and associated permeability.

Figure 3:
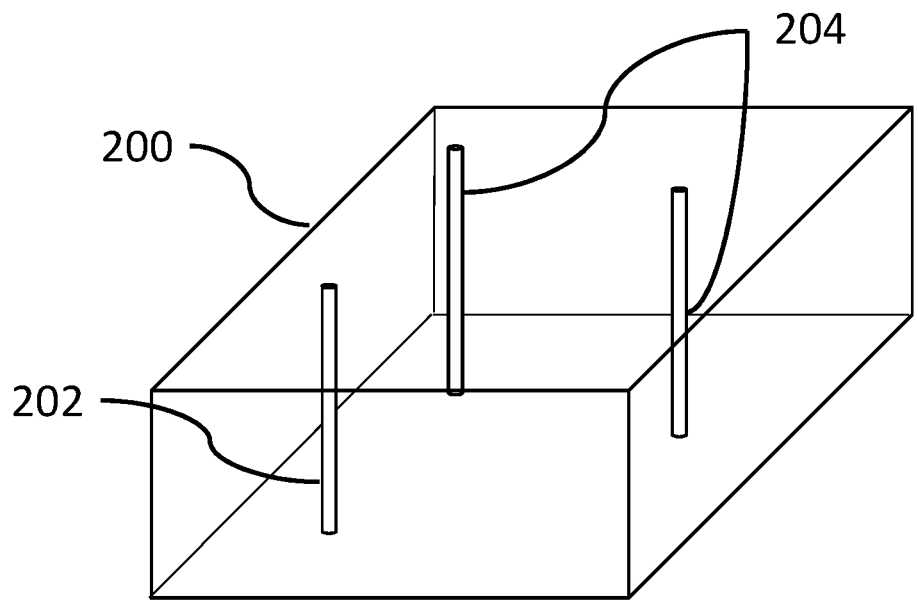
FIG. 3 illustrates field-scale rock fabric data at multiple well locations within a formation volume.
Figure 4:
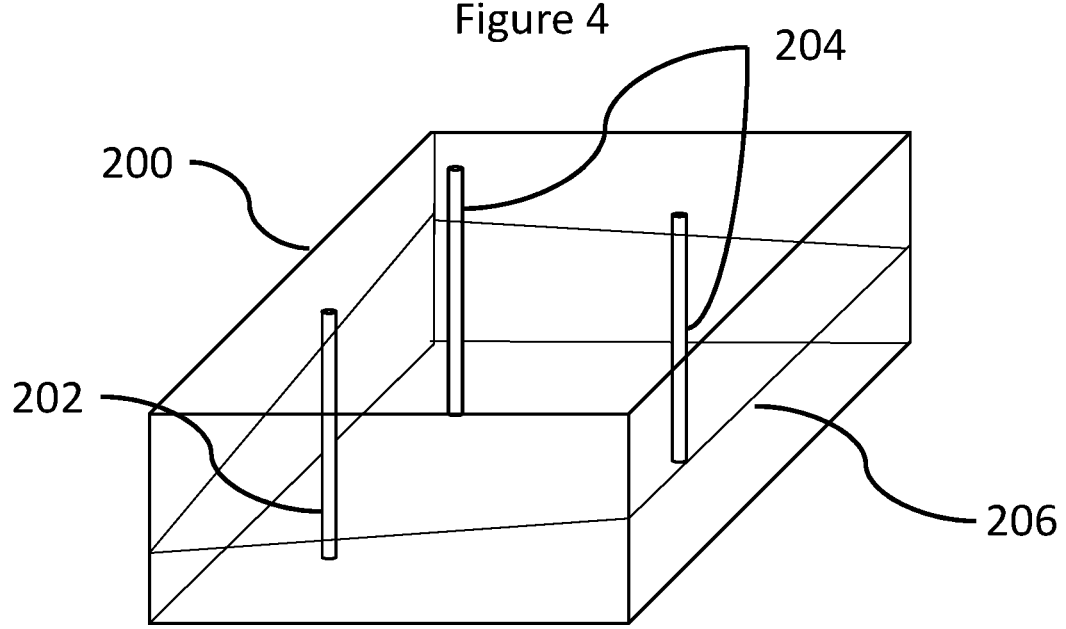
FIG. 4 illustrates the propagation of data between well locations within a formation volume.

Referring now to FIGS. 3 and 4, a formation volume 200 may include a cored well 202 for which a lab-scale resolution model is available and multiple logged wells 204 for which only field-scale data is available. Once the lab-scale rock fabric data is converted into field-scale rock fabric data (step 120 of FIG. 1) for cored well 202 the correlation between the field-scale rock fabric data and other field-scale data for cored well 202 can be determined (step 130 of FIG. 1). Because field-scale data is known at the logged wells 204, the field-scale rock fabric data at those wells can be determined by applying the determined correlation from the cored well 202 to the logged wells 204. The rock-fabric data can be interpolated between all of the wells 202, 204 so as to determine the rock-fabric data at any location, or along any contour 206 within the formation volume 200.

Once the geomodel, which includes rock fabric and associated permeability data, is built, it can be used for a variety of purposes. The geomodel can be used to visualize regions with high permeability so that landing points and completions can be placed in advantageous locations within the formation. The geomodel can also provide input data for the simulation of various processes that occur during acreage development. For example, the geomodel can be used to simulate (i) fluid leak-off during hydraulic fracturing, (ii) the lateral movement of fluid and the fluid's interaction with other wells during hydraulic fracturing, (iii) the effect of the fluid movement on fracture propagation from subsequent wells, and (iv) the deliverability of oil and water during production.

As the acreage represented by the geomodel is developed, additional core samples or field-scale logs can be taken to further refine and/or verify the operation of the geomodel and other models. The additional samples can also be used to identify and quantify changes in the rock fabric and associated properties that occur as the acreage is developed.

What is claimed is:

1. A method for simulating the movement of fluid through a formation volume comprising:
defining a lab-scale model representing rock fabric and associated permeability along a single well location within a formation volume;
converting the lab-scale model to a field-scale model representing rock fabric and associated permeability at the single well location;
correlating the field-scale model representing rock fabric and associated permeability with field-scale log data;
defining a field-scale model representing rock fabric and associated permeability at other well locations within the formation volume using field-scale log data from the other well locations;
interpolating the field-scale model representing rock fabric and associated permeability between the single well location and the other well locations so as to define a field-scale model representing rock fabric and associated permeability across the formation volume; and
simulating the movement of fluid through the formation volume.

2. The method of claim 1 wherein defining a lab-scale model representing rock fabric and associated permeability further comprises:
measuring a plurality of properties along a core sample at lab-scale resolution;
identifying and classifying a plurality of layers and interfaces along the core sample;
associating a permeability to each of the plurality of layer and interface classifications; and
integrating the plurality of measured properties with the plurality of layer and interface classifications and associated permeability to create the lab-scale model representing rock fabric and associated permeability.

3. The method of claim 2, wherein the plurality of properties include one or more of computed tomography density; gamma ray density, electrical resistivity, acoustic velocity, gamma ray components, magnetic susceptibility, rock hardness, and X-ray fluorescence elemental composition.

4. The method of claim 1, wherein the field-scale log data includes one or more of electrical properties, sonic properties, nuclear measurements, and pressure measurements.

5. The method of claim 1, wherein the movement of fluid through the formation is simulated during a completion operation.

6. The method of claim 1, wherein the movement of fluid through the formation is simulated during production.

7. The method of claim 1, further comprising updating the lab-scale model of the formation volume based on the movement of fluid through the formation volume.

8. A method for simulating the movement of fluid through a formation volume comprising:
defining a lab-scale rock fabric model at a single well location within a formation volume, wherein the lab-scale rock fabric model includes permeability per unit depth;
converting the lab-scale rock fabric model to a field-scale rock fabric model, wherein the field-scale rock fabric model includes permeability per unit depth;
correlating the field-scale rock fabric model with field-scale log data;

interpolating the field-scale rock fabric model across the formation volume using field-scale log data at other well locations within the formation volume; and simulating the movement of fluid through the formation volume.

9. The method of claim 8 wherein defining a lab-scale rock fabric model further comprises:

measuring a plurality of properties along a core sample at lab-scale resolution;

identifying and classifying a plurality of layers and interfaces along the core sample;

associating a permeability to each of the plurality of layer and interface classifications; and integrating the plurality of measured properties with the plurality of layer and interface classifications and associated permeability to create the lab-scale rock fabric model.

10. The method of claim 9, wherein the plurality of properties include one or more of computed tomography density; gamma ray density, electrical resistivity, acoustic velocity, gamma ray components, magnetic susceptibility, rock hardness, and X-ray fluorescence elemental composition.

11. The method of claim 8, wherein the field-scale log data includes one or more of electrical properties, sonic properties, nuclear measurements, and pressure measurements.

12. The method of claim 8, wherein the movement of fluid through the formation is simulated during a completion operation.

13. The method of claim 8, wherein the movement of fluid through the formation is simulated during production.

14. The method of claim 8, further comprising updating the lab-scale rock fabric model based on the movement of fluid through the formation volume.

15. A method for simulating the movement of fluid through a formation volume comprising:

measuring a plurality of properties along a core sample at lab-scale resolution;

identifying and classifying a plurality of layers and interfaces along the core sample;

associating a permeability to each of the plurality of layer and interface classifications;

integrating the plurality of measured properties with the plurality of layer and interface classifications and associated permeability to create a lab-scale rock fabric model;

converting the lab-scale rock fabric model to a field-scale rock fabric model at a single well location;

correlating the field-scale rock fabric model with field-scale log data;

defining the field-scale rock fabric model at other well locations within the formation volume using field-scale log data from the other well locations;

interpolating the field-scale rock fabric model between the single well location and the other well locations so as to model field-scale rock fabric across the formation volume; and simulating the movement of fluid through the formation volume.

16. The method of claim 15, wherein the plurality of properties include one or more of computed tomography density; gamma ray density, electrical resistivity, acoustic velocity, gamma ray components, magnetic susceptibility, rock hardness, and X-ray fluorescence elemental composition.

17. The method of claim 15, wherein the field-scale log data includes one or more of electrical properties, sonic properties, nuclear measurements, and pressure measurements.

18. The method of claim 15, wherein the movement of fluid through the formation is simulated during a completion operation.

19. The method of claim 15, wherein the movement of fluid through the formation is simulated during production.

20. The method of claim 15, further comprising updating the lab-scale rock fabric model based on the movement of fluid through the formation volume.

* * * * *